US00PP28411P2

(12) United States Plant Patent
Schrader

(10) Patent No.: US PP28,411 P2
(45) Date of Patent: Sep. 19, 2017

(54) ***GOMPHRENA* PLANT NAMED 'COSMIC FLARE'**

(50) Latin Name: *Gomphrena globosa*
Varietal Denomination: Cosmic Flare

(71) Applicant: Dennis A. Schrader, Mattituck, NY (US)

(72) Inventor: Dennis A. Schrader, Mattituck, NY (US)

(73) Assignee: LANDCRAFT ENVIRONMENTS, LTD, Mattituck, NY (US)

( * ) Notice: Subject to any disclaimer, the term of this patent is extended or adjusted under 35 U.S.C. 154(b) by 101 days.

(21) Appl. No.: 14/756,353

(22) Filed: Sep. 1, 2015

(51) Int. Cl.
*A01H 5/02* (2006.01)

(52) U.S. Cl.
USPC ..... Plt./263.1

(58) Field of Classification Search
USPC ..... Plt./263.1, 226
CPC ..... A01H 5/02
See application file for complete search history.

(56) References Cited

PUBLICATIONS https://issuu.com/angelatreadwell-palmer/docs/magazine0615web_final (2015 Plants Nouveau Introductions Magazine); Jun. 24, 2015, 0 pages.*

* cited by examiner

*Primary Examiner* — Kent L Bell
(74) *Attorney, Agent, or Firm* — Penny J. Aguirre

(57) ABSTRACT

A new cultivar of *Gomphrena* plant named, 'Cosmic Flare' that is characterized by its yellow-green foliage and its large inflorescences.

2 Drawing Sheets

Botanical classification: *Gomphrena globosa.*
Varietal denomination: 'Cosmic Flare'.

BACKGROUND OF THE INVENTION

The present invention relates to a new and distinct cultivar of *Gomphrena globosa* that will be referred to hereafter by its cultivar name, 'Cosmic Flare'. 'Cosmic Flare' represents a new cultivar of globe amaranth that is grown as an annual for landscape and container use.

The new cultivar was discovered by the Inventor as a chance seedling in a container that had been planted with seeds collected from an unnamed and unpatented plant of *Gomphrena globose* in Mattituck, N.Y. in spring of 2014.

Asexual propagation of the new cultivar was first accomplished by softwood stem cuttings by the Inventor in Mattituck, N.Y. in June of 2014. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Cosmic Flare' as a unique cultivar of *Gomphrena.*

1. 'Cosmic Flare' exhibits yellow-green foliage.
2. 'Cosmic Flare' exhibits large inflorescences.

The female parent plant of 'Cosmic Flare' differs from 'Cosmic Flare' in having foliage that is green in color. 'Cosmic Flare' can also be compared to the *Gomphrena globose* cultivars 'Buddy Purple' (not patented) and 'Cissy' (not patented). 'Buddy Purple' is similar to 'Cosmic Flare' in branching and inflorescence shape. 'Buddy Purple' differs from 'Cosmic Flare' in having a shorter plant height, in having green foliage, and in having inflorescences that are more compact and smaller in size. 'Cissy' is similar to 'Cosmic Flare' in inflorescence shape. 'Cissy' differs from 'Cosmic Flare' in having a much shorter plant height, a much more compact plant habit, in having green foliage, and in having inflorescences that are smaller in size.

BRIEF DESCRIPTION OF THE DRAWINGS

The accompanying colored photographs illustrate the overall appearance and distinct characteristics of the new *Gomphrena.* The photographs were taken of a plant 2 months in age as grown outdoors in a 30-cm container in West Newbury, Mass.

The photograph in FIG. 1 provides a side view of the plant habit of 'Cosmic Flare'.

Figure 1:
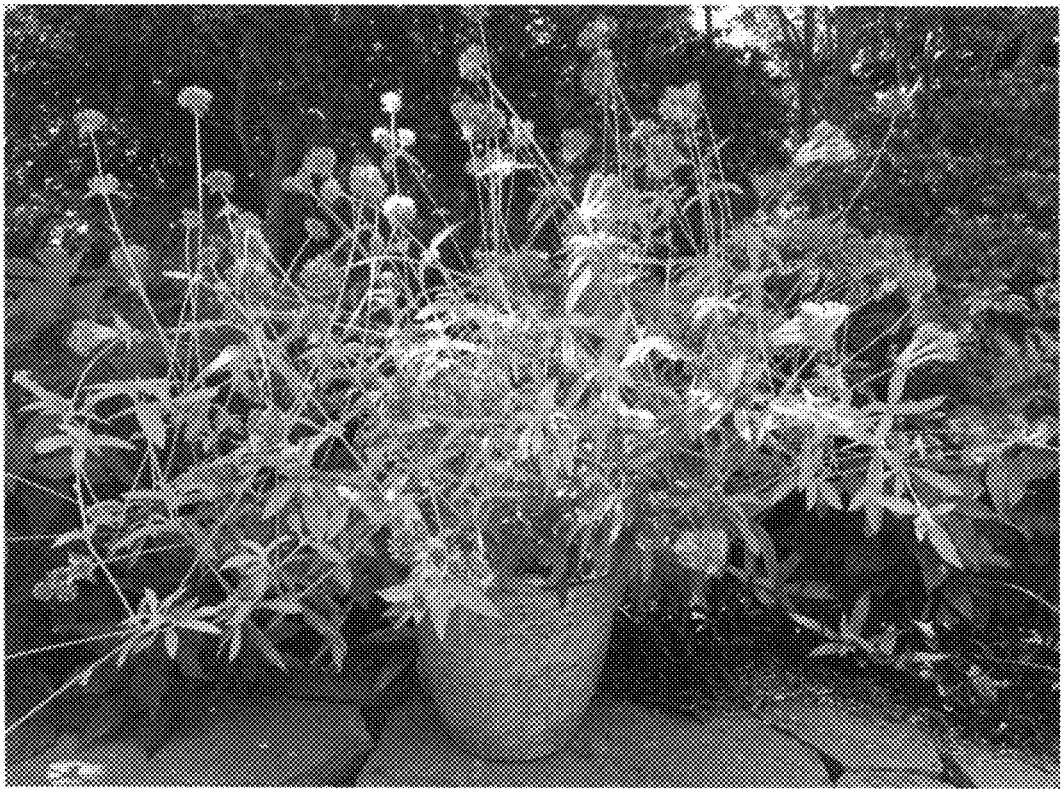
Figure 2:
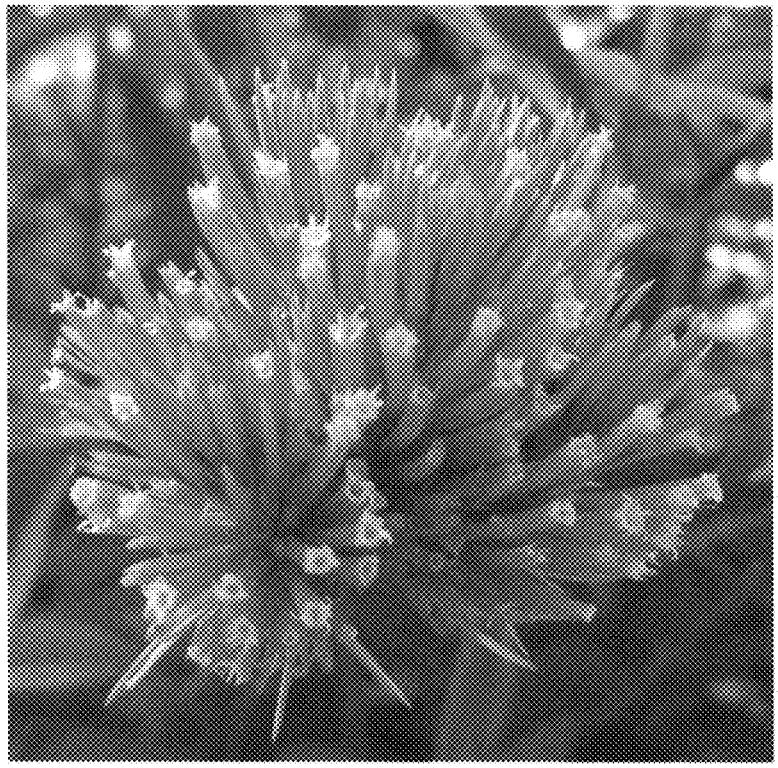

The photograph in FIG. 2 provides a close-up view of an inflorescence of 'Cosmic Flare'.

Figure 3:
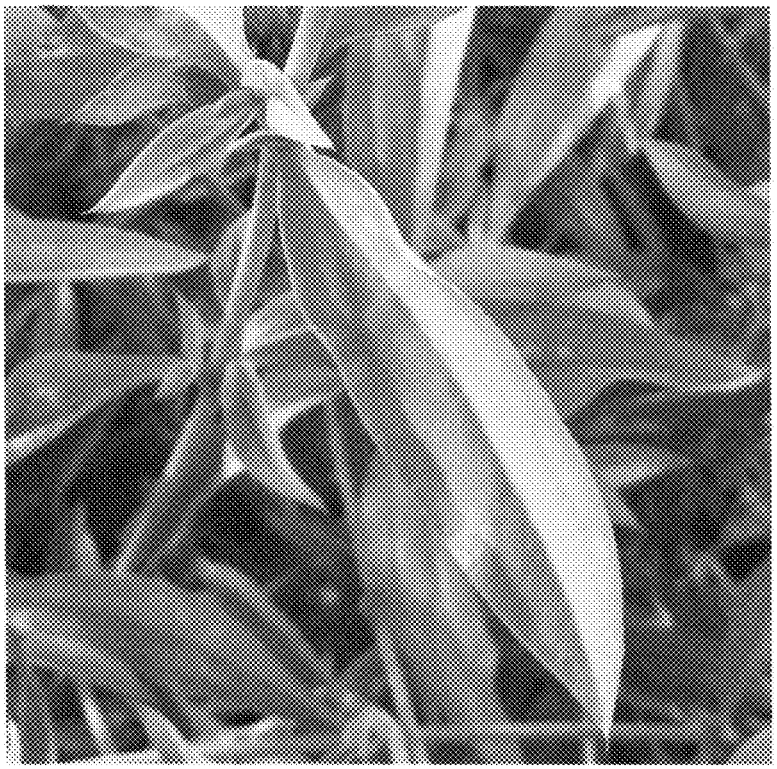

The photograph in FIG. 3 provides a close-up of the foliage of 'Cosmic Flare'.

The colors in the photographs are as close as possible with the photographic and printing technology utilized and the color values cited in the Detailed Botanical Description accurately describe the colors of the new *Gomphrena.*

DETAILED BOTANICAL DESCRIPTION

The following is a detailed description of plants 2 months in age as grown in 30-cm containers outdoors in West Newbury, Mass. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Spring to fall, flowers year round at temperatures of 24 to 35° C.

*Plant type*.—Annual.

*Plant habit*.—Upright, slightly spreading, freely branching.

*Height and spread*.—61 to 91 cm in height and 30 to 41 cm in spread.

*Diseases and pests*.—No susceptibility or resistance to pests and diseases has been observed.

*Root description*.—Fibrous.

*Propagation*.—Softwood stem cuttings.

*Time required for root development*.—Cutting root in five to six weeks in 98-cell plugs at 24° C. with rooting inducing solution and mist.

*Time to bloom from propagation*.—6 to 8 weeks.

*Growth rate*.—Vigorous.

Stem description (main branches and lateral branches):

*Stem color*.—Young and mature stems; 145A with anthocyanin coloration of 186B.

*Stem size*.—Main stems; numerous, average of 20 cm in length and an average of 2 mm in diameter, lateral branches; 5 per stem, an average of 15 cm in length and 3 mm in diameter.

*Branching habit*.—Numerous main stems with 5 lateral branches per stem.

*Stem shape*.—Rounded.

*Stem surface*.—Dull and sparsely pubescent with short hairs N155A in color.

*Stem aspect*.—Moderately strong, held horizontal to outward.

*Internode*.—Average of 12 cm in length.

Foliage description:

*Leaf division*.—Single.

*Leaf attachment*.—Sessile.

*Leaf arrangement*.—Opposite.

*Leaf number*.—Average of 12 (6 pairs) on basal stem 20 cm in length.

*Leaf shape*.—Lanceolate.

*Leaf apex*.—Acute.

*Leaf surface*.—Upper and lower surface dull and moderately covered with pubescence N155A in color and up to 1.5 mm in length.

*Leaf base*.—Decurrant.

*Leaf venation*.—Pinnate, color matches leaf coloration, veins on lower surface are pubescent.

*Leaf margin*.—Entire.

*Leaf color*.—Upper surface 153D, lower surface between 154B and 153C.

*Leaf size*.—Average of 10 cm in length and 2.5 cm in width.

Flower description:

*Inflorescence type*.—Small, globose-shaped bracts; small flat flowers arranged in dense, globose, papery textured clover-like flower heads, flowers are upright and outwardly facing; flowers are sessile with a single two-parted perianth; inflorescence heads are subtended by two small flower bracts.

*Inflorescence size*.—Average of 2.5 cm in height and 1.5 cm in width.

*Inflorescence color*.—N78B.

*Flower fragrance*.—None.

*Flower quantity*.—Average of 150 per plant, up to 100 per inflorescence.

*Flower lastingness*.—Average of 4 weeks.

*Flower buds*.—Lanceolate in shape, average of 9 mm in diameter and 5 mm in length, 68C in color, surface is dull.

*Flower habit*.—Freely flowering.

*Flower shape*.—Tubular.

*Flower size*.—An average of 1.2 cm in depth and 1 mm in diameter.

*Perianth segments*.—Five segments in a single flattened whorl, lanceolate, acute Apex, truncate base, entire margin, about 1.2 cm in length: and 2 mm in width, texture, upper and lower surfaces smooth and glabrous, color when opening and mature upper and lower surfaces N78B.

*Sepals*.—None observed.

*Peduncles*.—Average of 6 cm in length and 2 mm in width, strong, held mostly upright, N144D in color, surface texture is dull and moderately covered with pubescence N155A in color and up to 1 mm in length.

*Bracts*.—2, opposite, 1.5 cm in length, 1.1 mm in width, lanceolate in shape, acute apex, dull and glabrous surfaces, upper and lower surface; N144D in color.

Reproductive organs:

*Gynoecium*.—1 pistil, average of 6 mm in length, stigma is bi-parted, 145C in color, and 5 mm in length, style is an average of 5 mm in length, 145C in color, ovary is an average of 1 mm in diameter and 149C in color.

*Androecium*.—5 stamens, 4 mm in length and N155A in color, anthers are an average of 5 mm in length and 155A in color, filaments are an average of 3 mm in length and 145C in color, pollen is sparse in quantity and 155A in color.

*Fruit and seed*.—No fruit or seed have been observed.

It is claimed:

1. A new and distinct cultivar of *Gomphrena* plant named 'Cosmic Flare' as herein illustrated and described.

* * * * *